(12) United States Patent
Baltes et al.

(10) Patent No.: US 8,569,546 B2
(45) Date of Patent: Oct. 29, 2013

(54) OXIDATIVE DEHYDROGENATION OF METHANOL TO FORMALDEHYDE OVER SILVER-CONTAINING KNITS

(75) Inventors: Christian Baltes, Neustadt (DE); Grigorios Kolios, Neustadt (DE); Peter Resch, Hettenleidelheim (DE); Ulrike Wegerle, Worms (DE); Torsten Mäurer, Lambsheim (DE)

(73) Assignee: BASF SE (DE)

( * ) Notice: Subject to any disclaimer, the term of this patent is extended or adjusted under 35 U.S.C. 154(b) by 3 days.

(21) Appl. No.: 13/455,593

(22) Filed: Apr. 25, 2012

(65) Prior Publication Data

US 2012/0277473 A1 Nov. 1, 2012

Related U.S. Application Data

(60) Provisional application No. 61/478,950, filed on Apr. 26, 2011.

(51) Int. Cl.
*C07C 45/27* (2006.01)
(52) U.S. Cl.
USPC ........................................................ 568/449
(58) Field of Classification Search
USPC ........................................................ 568/449
See application file for complete search history.

(56) References Cited

U.S. PATENT DOCUMENTS

| 4,076,754 A | 2/1978 | Kiser et al. |
| 4,418,215 A | 11/1983 | Jenkins |

FOREIGN PATENT DOCUMENTS

| DE | 1136318 B | 9/1962 |
| DE | 1235881 B | 3/1967 |
| DE | 1277834 B | 9/1968 |
| DE | 2829035 A1 | 1/1980 |
| DE | 3047193 A1 | 9/1981 |
| GB | 941642 A | 11/1963 |
| GB | 1135476 A | 12/1968 |
| GB | 1188215 A | 4/1970 |

OTHER PUBLICATIONS

Ullmann's Encyclopedia of Industrial Chemistry, vol. 15, 6th Edition, (2003), pp. 1-34.

*Primary Examiner* — Sikarl Witherspoon
(74) *Attorney, Agent, or Firm* — Novak Druce Connolly Bove + Quigg LLP

(57) ABSTRACT

In a process for producing $C_1$-$C_{10}$ aldehydes by oxidative dehydrogenation of $C_1$-$C_{10}$ alcohols over a shaped catalyst body obtainable by three-dimensional shaping and/or arranging in space of silver-containing fibers and/or threads, the average diameter or the average diagonal length of an essentially rectangular or square cross section of these silver-containing fibers and/or threads is in the range from 30 μm to 200 μm.

13 Claims, 1 Drawing Sheet

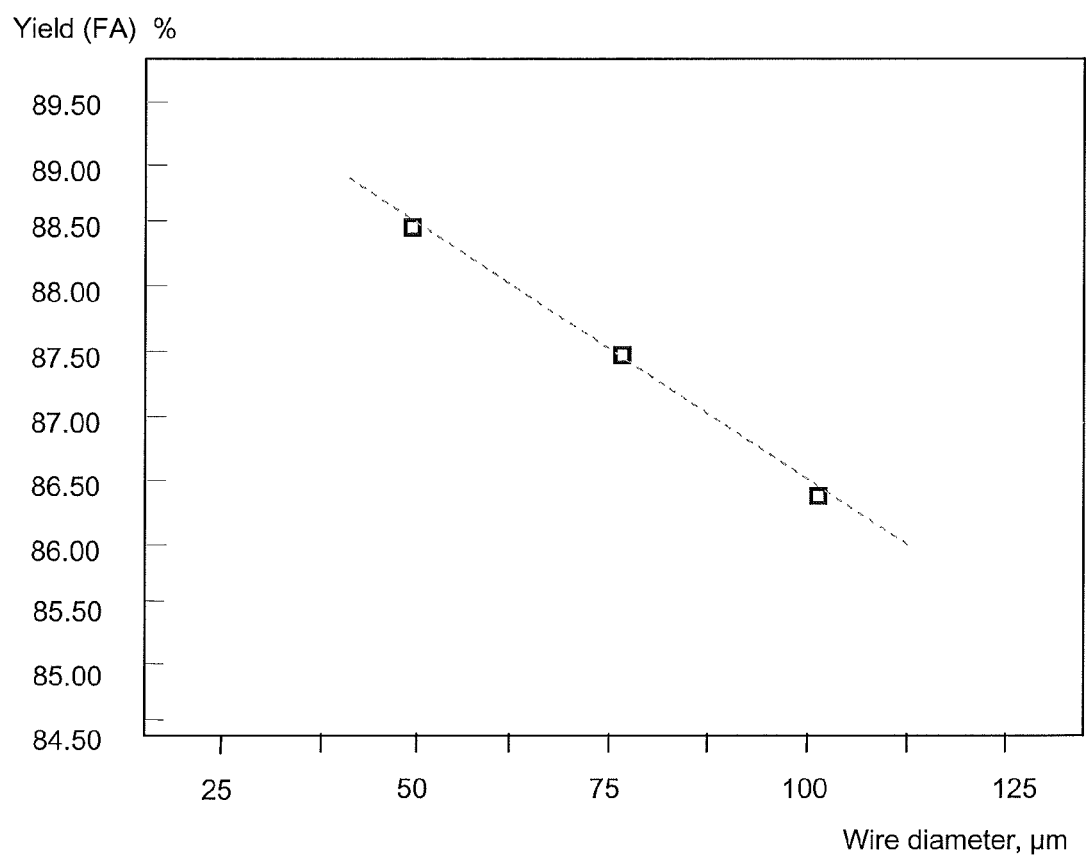

OXIDATIVE DEHYDROGENATION OF METHANOL TO FORMALDEHYDE OVER SILVER-CONTAINING KNITS

CROSS-REFERENCE TO RELATED APPLICATIONS

This application claims benefit (under 35 USC 119(e)) of U.S. Provisional Application 61/478,950, filed Apr. 26, 2011, which is incorporated by reference.

BACKGROUND OF THE INVENTION

The present invention relates to a process for producing $C_1$-$C_{10}$ aldehydes by oxidative dehydrogenation of $C_1$-$C_{10}$ alcohols over a shaped catalytst body which comprises shaped silver-containing fibers and/or threads, wherein the average diameter of these silver-containing fibers and/or threads is in the range from 30 μm to 200 μm.

The process for producing formaldehyde by oxidation/dehydrogenation of methanol over a silver catalyst is long known, see for example Ullmann's Encyclopedia of Industrial Chemistry, 2005, pages. 1 ff.

The silver catalyst used can be used in various forms. For example as granular crystalline silver but also in the form of silver nets or silver gauze.

U.S. Pat. No. 4,076,754 (Du Pont) describes a two-stage process for the manufacture of formaldehyde from methanol, air and water. The catalyst used comprises 40 superposed sheets of 20 mesh silver gauze (i.e., mesh size 1.25 mm) made from silver wire 0.014 inch (i.e., 350 μm or 0.35 mm) in diameter. The density or the void fraction of the silver gauze is not disclosed in U.S. Pat. No. 4,076,754.

DE 2829035 A1 (Heraeus) describes a catalyst comprising catalytically active metallic fibers which consist of silver, platinum, rhodium, palladium or an alloy based on one thereof, wherein the metallic fibers are interconnected feltlike in the manner of a needle-bonded composite. The catalyst can be used for ammonia oxidation and the manufacture of hydrocyanic acid or formaldehyde. The cross section of a ribbon-shaped fiber can be rectangular with the dimensions of 100 μm and 50 μm, the length can be between 10 cm and 1 m. The density or the void fraction of the interfelted metallic fiber body is not described.

DE 3047193 A1 (Johnson Matthey) describes a catalyst made of silver or a silver alloy. The catalyst body is produced by melt spun process or melt extraction process. For example, a ribbon 1 to 2 mm in width and 50 to 60 μm in thickness is processed by crimping and cutting to yield undulating catalyst bodies about 1 cm in length and hence rather short-fibered. DE 3047193 A1 does not disclose a braid, knit, felt or the like formed from these catalyst bodies.

Although the catalytic oxidation/dehydrogenation of alcohols to aldehydes, more particularly methanol to formaldehyde, is already long known, there is still room for improvement, for example an increase in catalytic activity, in formaldehyde selectivity, advantageously for unchanged catalytic activity, or in the pressure drop over the catalyst.

Applicant studies have shown, particularly with regard to the oxidative dehydrogenation of methanol to formaldehyde, that it is not a straightforward matter to use fiber- or wire-containing structures as catalysts. This is because the constitution of the shaped catalyst body has to make it possible to establish a stable ignited reaction zone under the operating conditions of the industrial process for example of the oxidative dehydrogenation of methanol to formaldehyde. However, the current state of the art does not disclose the requisite features of such a shaped catalyst body.

A SUMMARY OF THE INVENTION

The problem addressed by the present invention was that of improving the aldehyde yield of the oxidative dehydrogenation of alcohols to aldehydes, more particularly methanol to formaldehyde, by using a shaped catalyst body comprising shaped silver-containing fibers and/or threads.

BRIEF DESCRIPTION OF THE FIGURES

FIG. 1 illustrates the parameters of Examples 1 to 3.

A DETAILED DESCRIPTION OF THE INVENTION

Useful $C_1$-$C_{10}$ alcohols include alcohols having 1 to 10 carbon atoms and one or more, preferably two to three, OH groups. The alcohols preferably have one or two OH groups. The alcohols may be aliphatic, linear, branched or cyclic, comprise one or more C—C double or triple bonds in the molecule, they may be aralyk or alkylaryl alcohols. They are preferably primary alcohols or in the case of polyhydric alcohols vicinal $C_1$-$C_{10}$ diols.

Examples of the $C_1$-$C_{10}$ alcohols mentioned are methanol, ethanol, 1-propanol, isopropanol, n-butanol, isobutanol, sec-butanol, tert-butanol, 1,2-ethanediol, 1,2-propanediol, allyl alcohol, prenol, isoprenol. Methanol is particularly preferred.

Useful $C_1$-$C_{10}$ aldehydes include the aldehydes obtainable from the abovementioned $C_1$-$C_{10}$ alcohols by oxidative dehydrogenation. The aldehydes may have one or more aldehyde groups in the molecule, preferably they have one or two aldehyde groups in the molecule. Examples of $C_1$-$C_{10}$ aldehydes that are in accordance with the present invention are formaldehyde (methanal), glyoxal (HCO—CHO), prenal or isoprenal.

In a particularly preferred embodiment, the process of the present invention is used for producing formaldehyde (methanal) from methanol, as described in what follows. However, this methanol oxidation process can also be carried out in analogous form for the abovementioned $C_1$-$C_{10}$ aldehydes.

Suitable starting materials for the methanol oxidation process are pure methanol, technical grade methanol, crude methanol produced by high or low pressure process, or advantageously mixtures thereof with water; the methanol concentration of the aqueous mixtures in the starting material is advantageously in the range from 60% to 95% by weight and preferably in the range from 70% to 90% by weight. An advantageous embodiment uses crude methanol purified according to the processes described in DE-B-12 77 834, DE-C-12 35 881 and DE-C11 36 318 by removal of a lower-boiling fraction or, respectively, by treatment with oxidizing agents and/or alkalis.

The methanol is fed to the reactor space in vapor form, advantageously admixture with water vapor and optionally with an inert gas. Nitrogen is useful as an inert gas for the process for example.

The oxidizing agent used can be not only pure oxygen but also preferably oxygen-containing gases, more particularly air. Oxygen and methanol are advantageously used in a molar ratio of 0.25 to 0.6 and more particularly 0.35 to 0.5 mol of oxygen per mol of methanol. The total amount of water vapor is preferably not more than 3.0, and advantageously 0.67 to 1.75 mol per mol of methanol.

In the industrial operation of the formaldehyde process, the reaction mixture described above is generally introduced into the reactor at a temperature between 50° C. and 200° C. and also typically at an absolute pressure between 1 bar and 2 bar.

The starting materials mentioned are then typically passed into one or more zones wherein the shaped catalyst body of the present invention is situated.

The shaped catalyst body of the present invention is a three-dimensional construct obtainable by three-dimensional shaping and/or arranging in space of silver-containing fibers or silver-containing threads.

The silver-containing fibers or threads comprise silver in an amount ranging from 50% by weight to 100% by weight, preferably from 90% by weight to 100% by weight and more preferably from 98% by weight to 100% by weight, and further metals of the 10th or 11th group of the periodic table, preferably metals selected from the group consisting of copper, palladium, titanium in the range from 0% by weight to 50% by weight, preferably from 0% by weight to 10% by weight and more preferably from 0% by weight to 2% by weight.

Highly suitable silver-containing fibers or threads comprise virtually 100% by weight of silver.

Silver-containing fibers in accordance with the present invention are generally from about 1 mm to 100 mm in length, while silver-containing threads which are in accordance with the present invention can be infinite in theory while in practice they generally have a length in the range from a few centimeters up to several kilometers.

The average diameter (in the case of an essentially round cross section) or the average diagonal length (in the case of an essentially rectangular or square cross section) of the silver-containing fibers or threads is in the range from 30 to 200 μm, preferably in the range from 30 to 150 μm and more preferably in the range from 30 to 70 μm.

The average diameter or the average diagonal length is determined using the method of DIN ISO 4782 "Nominal Wire Diameters for Woven Screens".

Silver-containing fibers or threads are known to a person skilled in the art, are commercially available and are used for example as an electrical conductor material, in high value textiles or in corrosion-resistant sensory applications (pH determination for example).

The three-dimensional shaping and/or arranging of the silver-containing fibers or threads in space can be effected with or without order.

Shaping and/or arranging the silver-containing fibers which are in accordance with the present invention or preferably silver-containing threads which are in accordance with the present invention without order typically leads to so-called clews. They are obtainable for example by fibers or wires to form a statistically nonuniformly arranged clew and then are further compressed, using various pressures, to the desired clew density or the desired void fraction in the clew.

In such clews, the silver-containing fibers or threads which are in accordance with the present invention are arranged in space without regularity, and can also be interengaged with each other feltlike and thereby acquire their particular mechanical stability for example. Clews of this kind are hereinafter also referred to as "inventive silver-containing clews".

The shaping and/or arranging of the silver-containing fibers or threads with order leads to essentially regular and ordered structures having periodically repeating unit cells, for example meshes or holes. Highly suitable processes for shaping and/or arranging the silver-containing fibers or preferably threads in space with order is knitting or weaving or the like and subsequent densifying.

Highly suitable ordered structures formed from silver-containing fibers or preferably silver-containing threads are so-called knits or nets, for example having a mesh size in the range from 300 to 50 mesh (80 μm to 500 μm], preferably in the range from 300 to 100 mesh (80 μm to 250 μm). These knits or nets are hereinafter also referred to as "inventive silver-containing knits".

The density of inventive silver-containing knits or inventive silver-containing clews is generally in the range from 2 $g/cm^3$ to 4 g/cm $g/cm^3$ and preferably in the range from 3 $g/cm^3$ to 4 $g/cm^3$.

The density generally corresponds to a void fraction in the inventive silver-containing knits or inventive silver-containing clews ranging from 60% to 80% and preferably from 60% to 75%.

A void fraction of more than 80% is disadvantageous. The inventive void fraction of the inventive silver-containing knits or inventive silver-containing clews is also advantageous to ensure an "ignition" of the catalytic oxidation/dehydrogenation of the methanol at very low temperatures, for example 350° C. or less and advantageously in the range from 200 to 350° C. Typically, the inventive silver-containing knit or the inventive silver-containing clew is preheated until the reaction (oxidative dehydrogenation of methanol to formaldehyde) lights off. Thereafter, the reaction mentioned is generally self-sustaining under adiabatic conditions.

The abovementioned density and the void fraction of the inventive silver-containing knits or inventive silver-containing clews is determined with the method as follows: A body of known geometry is weighed. The ratio of its weight to the volume occupied by it determines the density. The ratio to the weight of a geometrically identical massive body composed of the same material defines the void fraction.

The shaped catalyst body of the present invention can be present in manifold spatial form.

For example, the inventive silver-containing clews forming the shaped catalyst body of the present invention or preferably the inventive silver-containing knits can be present as mats or disks, i.e., as sheetlike constructs whose lengths and widths are many times greater than their heights. Optionally, a plurality of shaped bodies can be present stacked on top of each other or put together in segment fashion.

For example, the inventive silver-containing clews forming the shaped catalyst body of the present invention or preferably the inventive silver-containing knits can also be present as Raschig rings and/or as helices.

The absolute measurements of the shaped catalyst bodies of the present invention generally depend on the dimensions of the reactor in which the shaped catalyst body is used.

Exemplary dimensions for the shaped catalyst bodies of the present invention range from 120 to 30 cm in length, from 50 to 10 cm in width and from 1 to 10 cm and preferably from 2 to 4 cm in height.

The geometric shape of the shaped catalyst body of the present invention is generally variable.

Preference is given to rectangular/cuboid or round/roundel-shaped or cylindrical catalyst body of the abovementioned dimensions, and the diameter of the round catalyst body is for example in the range from 2 cm to 300 cm, preferably in the range from 25 cm to 300 cm and more preferably in the range from 50 cm to 300 cm.

Typically, the shaped catalyst body is used in the reaction space, wherein the abovementioned starting materials, for example alcohol, such as methanol, oxygen-containing gas, are reacted, resting on a carrier device.

Such carrier devices are known, for example grids, baskets or perforate plates or stable nets of diverse materials, preferably of metals, for example stainless steel or silver.

The shaped catalyst body of the present invention can be present as sole catalytically active constituent in the reaction zone in which the abovementioned starting materials/streams comprising methanol, oxygen and water are used. However, the shaped catalyst body of the present invention can also be present in the presence of granular silver catalysts and/or other catalysts for the oxidative dehydrogenation of the alcohols to aldehydes.

For example, a layered structure of shaped catalyst bodies according to the present invention//granular silver catalysts can be present.

It is also possible to use a plurality of reaction zones in which the abovementioned starting materials/streams, for example alcohol, such as methanol, oxygen-containing gas are used and which contain the catalyst of the present invention "connected in series". This connection in series can be actualized in one reactor or in a reactor cascade.

The process is otherwise carried out in a conventional manner by, for example, passing a gas mixture of methanol vapor, air, optionally inert gas and advantageously water vapor in aforementioned amounts at temperatures of about 550 to 750° C. and more particularly 595 to 710° C., through the reaction zone or zones containing the catalyst of the present invention. The process is generally carried out in a continuous operation at an absolute pressure between 0.5 and 2 bar and preferably between 1.2 and 1.8 bar. It is advantageous here for the reaction gases leaving the catalyst zone to be cooled down, for example to temperatures of 50 to 350° C., within a short time. After the gas mixture has cooled down, it is then advantageously fed to an absorption tower in which the formaldehyde is scrubbed with water out of the gas mixture, advantageously countercurrently.

The process is also more particularly described in Ullmann's Encyclopedia of Industrial Chemistry, 2005, pages 1 ff.

The advantages of the process according to the present invention are in particular:

An improved yield of $C_1$-$C_{10}$ aldehyde, especially formaldehyde, compared with conventional catalysts (higher selectivities to, for example, formaldehyde and, for example, comparable methanol conversions at lower catalyst mass).

An improved uniformity of the catalyst packing in respect of layer thickness and material density.

The possibility of influencing the catalytic properties of the shaped catalyst body of the present invention via the specific adjustment of the geometry of the shaped body, more particularly of the wire/fiber structure, concerning the diameter, and the density of the shaped body.

Surprisingly, relationships result between the geometric and structural parameters of the shaped catalyst bodies and the enhanced chemical productivity. It was observed in this connection that in the oxidation dehydration of methanol, for example, the formaldehyde yield in a single pass through the catalyst bed increases with decreasing wire diameter. Moreover, an advantageous ignition behavior of the shaped catalyst body correlates with the packing density thereof.

EXAMPLES

Example 1

A gaseous water-methanol mixture having a molar ratio of water/methanol equal to 1.0 was mixed with air (140 NI/h) and nitrogen (50 NI/h) such that the molar ratio of methanol to oxygen was 2.5. This mixture was heated to 140° C. in a preheater upstream of the reactor, and subsequently passed through a knitted silver catalyst. This catalyst consisted of a shaped cylindrical body having a height of 10 mm and a diameter of 20 mm. The shaped body consisting of compressed silver wool having a fiber diameter of 0.05 mm (density of shaped body: 3 g/cm$^3$, void fraction: 75%). The runs were done adiabatically in a quartz glass reactor having an internal diameter of 20 mm. The adiabacy of the reactor was achieved through passive insulation, and completely dispenses with any compensatory heating. To ensure an ignition of the adiabatically performed reaction on the silver catalyst, the methanol-water-air-nitrogen mixture was heated to 300° C., at which temperatures the molar ratio of methanol/oxygen was 7:1 and nitrogen was metered at 300 NI/h. The adiabatic ignition ensued at 300° C. Then, the abovementioned composition of water/methanol/air/nitrogen was metered incrementally. On setting the metering and the preheater temperature as described above, the catalyst bed reached temperatures of 595° C. in the ignited adiabatic reaction. A weight hourly space velocity of 95 000 h$^{-1}$ over the catalyst was achieved. The product mixture emerging from the catalyst bed was cooled to 120° C. in a heat exchanger. The composition of the product mixture was analyzed by gas chromatography. Under the conditions mentioned, a methanol conversion of 99% and a formaldehyde selectivity of 90% were achieved. A conventionally used electrolytically produced granular silver catalyst (fraction size 0.5 to 2 mm) achieved a formaldehyde selectivity of 87% at a methanol conversion of 99%.

Example 2

Example 1 was repeated with regard to reactant metering and catalyst ignition. The catalyst used was a three-dimensional shaped cylindrical body made of compressed nets of silver. The diameter of the silver wire was 0.076 mm. The height of the shaped catalyst body was 20 mm and the diameter was 20 mm. Under the conditions mentioned, a methanol conversion of 98% and a formaldehyde selectivity of 90% were achieved. A conventionally used electrolytically produced granular silver catalyst (fraction size 0.5 to 2 mm) achieved a formaldehyde selectivity of 87% at a methanol conversion of 98%.

Example 3

Example 1 was repeated with regard to reactant metering and catalyst ignition. The catalyst used was a three-dimensional shaped cylindrical body made of a knitted and subsequently compressed wire of silver. The diameter of the silver wire was 0.1 mm. The density of the pressed knit was 3 g/cm$^3$. The height of the shaped catalyst body was 10 mm, the diameter was 20 mm. Under the conditions mentioned, a methanol conversion of 96% and a formaldehyde selectivity of 91% were achieved. A conventionally used electrolytically produced granular silver catalyst (fraction size 0.5 to 2 mm) achieved a formaldehyde selectivity of 90% at a methanol conversion of 96%.

Parameters of Examples 1 to 3 are depicted below in FIG. 1.

FIG. 1: dependence of catalyst performance (yield of formaldehyde, based on methanol) on diameter of wire used to form the shaped catalytic body. All the shaped bodies have the same volume and the same density. The reaction conditions are identical.

We claim:

1. A process for producing $C_1$-$C_{10}$ aldehydes by oxidative dehydrogenation of $C_1$-$C_{10}$ alcohols over a shaped catalyst body obtainable by three-dimensional shaping and/or arranging in space of silver-containing fibers and/or threads, wherein the average diameter or the average diagonal length of an essentially rectangular or square cross section of these silver-containing fibers and/or threads is in the range from 30 µm to 200 µm.

2. The process according to claim 1, wherein the $C_1$-$C_{10}$ aldehyde is formaldehyde and the $C_1$-$C_{10}$ alcohol is methanol.

3. The process according to claim 1, wherein the average diameter or the average diagonal length of an essentially rectangular or square cross section of these silver-containing fibers and/or threads is in the range from 30 µm to 150 µm.

4. The process according to claim 1, wherein the average diameter or the average diagonal length of an essentially rectangular or square cross section of these silver-containing fibers and/or threads is in the range from 30 µm to 70 µm.

5. The process according to claim 2, wherein the average diameter or the average diagonal length of an essentially rectangular or square cross section of these silver-containing fibers and/or threads is in the range from 30 µm to 70 µm.

6. The process according to claim 1, wherein the shaped silver-containing fibers and/or silver-containing threads have a density in the range from 2 $g/cm^3$ to 4 $g/cm^3$.

7. The process according to claim 1, wherein the three-dimensional shaping and/or arranging in space is effected with or without order.

8. The process according to claim 5, wherein the shaped silver-containing fibers and/or silver-containing threads have a density in the range from 2 $g/cm^3$ to 4 $g/cm^3$.

9. The process according to claim 5, wherein the three-dimensional shaping and/or arranging in space is effected with or without order.

10. The process according to claim 1, wherein the shaped silver-containing fibers and/or silver-containing threads are present without order and in the form of clews.

11. The process according to claim 1, wherein the shaped silver-containing fibers and/or silver-containing threads are present with order and in the form of knits or nets.

12. The process according to claim 5, wherein the shaped silver-containing fibers and/or silver-containing threads are present without order and in the form of clews.

13. The process according to claim 5, wherein the shaped silver-containing fibers and/or silver-containing threads are present with order and in the form of knits or nets.

* * * * *